United States Patent [19]

Gregory

[11] Patent Number: 4,758,598

[45] Date of Patent: * Jul. 19, 1988

[54] SOLID SHAPED ARTICLES

[75] Inventor: George K. E. Gregory, Marlow, England

[73] Assignee: John Wyeth & Brother Ltd., Maidenhead, England

[*] Notice: The portion of the term of this patent subsequent to Dec. 15, 1998 has been disclaimed.

[21] Appl. No.: 850,430

[22] Filed: Apr. 8, 1986

Related U.S. Application Data

[63] Continuation of Ser. No. 441,342, Nov. 15, 1982, abandoned.

[30] Foreign Application Priority Data

Dec. 2, 1981 [GB] United Kingdom ............... 8136360

[51] Int. Cl.$^4$ ................... A61K 47/00; A61K 9/26; B65D 85/56

[52] U.S. Cl. .................................. 514/774; 424/400; 424/464; 424/484

[58] Field of Search ............... 424/14, 400, 464, 484; 514/774

[56] References Cited

U.S. PATENT DOCUMENTS 4,305,502 12/1981 Gregory et al. ............... 206/532
4,371,516 2/1983 Gregory et al. ............... 424/22

Primary Examiner—Shep K. Rose
Attorney, Agent, or Firm—Arthur E. Wilfond; Richard A. Elder; Ronald W. Alice

[57] ABSTRACT

Solid shaped articles, particularly pharmaceutical dosage forms, are prepared by freezing in a mould a composition comprising a predetermined amount of chemical (e.g. pharmaceutical) and a solution of carrier material and then subliming solvent from the frozen composition. The side wall or walls of the mould make an angle with the vertical of at least 5° at the surface of the composition. This enables shaped articles of constant thickness to be produced with minimum sublimation times.

12 Claims, 1 Drawing Sheet

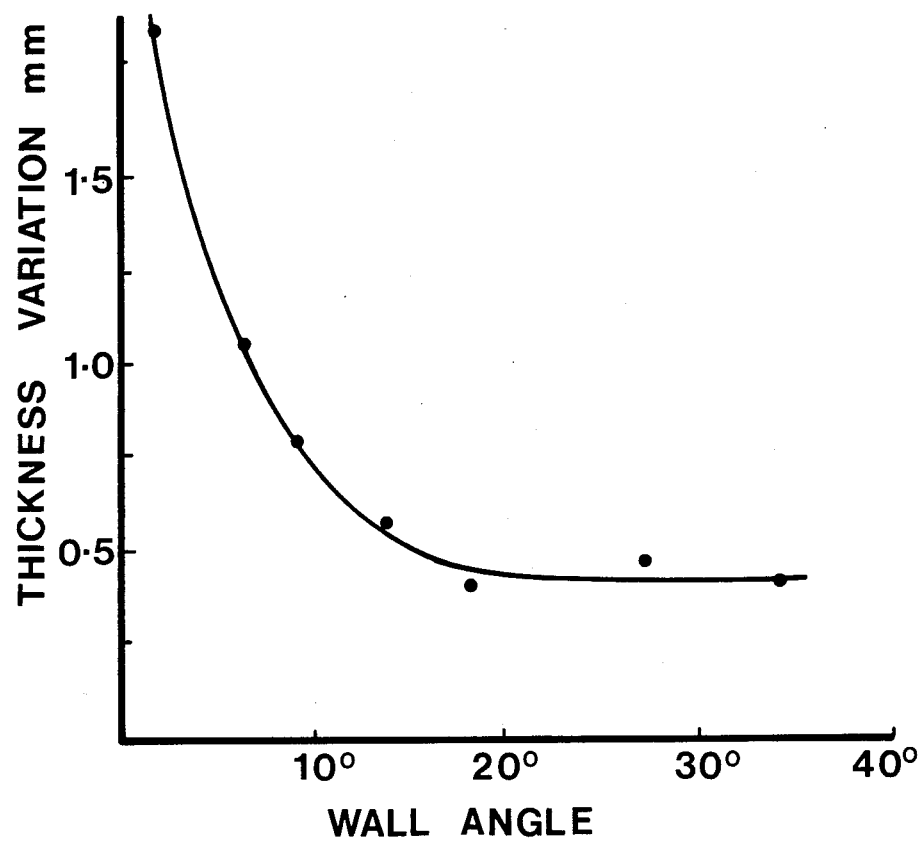

SOLID SHAPED ARTICLES

This application is a continuation of application Ser. No. 441,342 filed Nov. 15, 1982 now abandoned.

This invention relates to a solid shaped article carrying a predetermined unit quantity of chemical and to a novel process for preparing such an article.

It is known to produce shaped articles carrying chemicals by a process involving sublimation of a solvent from a composition in the solid state comprising the chemical and a solution in a solvent of a carrier material. Such a process is described, for example, in U.S. Pat. Nos. 4,305,502 and 4,371,516 claim priority from the same U.K. applications as French Pat. No. 2,366,835, and which issued as U.K. Pat. No. 1,548,022. The process generally involves freezing the composition in a mould and then freeze drying the frozen composition. The mould can be, for example, a depression in a metal plate but it is preferably a depression in a sheet of filmic material. The filmic material preferably contains more than one depression. The filmic material may be similar to that employed in conventional blister packs which are used for packaging oral contraceptive tablets and like medicament forms. For example the filmic material may be made of thermoplastic material with the depressions formed by thermoforming. The preferred filmic material is a polyvinyl chloride film. Laminates such as polyvinyl chloride/polyvinylidine chloride, polyvinyl chloride/polytetrafluoroethylene or polyvinyl chloride/polyvinylidene chloride/polyethylene may also be used.

Our investigations of the process described in the above mentioned specifications have shown that one of the rate limiting steps in the production of the shaped article, especially on a commercial scale, is the time required for sublimation of the solvent in the freeze drying apparatus. We have found that the drying time can be reduced substantially if the depth of the composition in the mould (prior to freezing) is kept to a minimum. In general, drying times tend to be proportional to the square of the thickness. We have found that if the mean depth of composition in the mould is about 4.0 mm or less (preferably about 3.5 mm or less) reasonable drying times can be attained. However, when shaped articles of this mean thickness were produced in conventional moulds with substantially vertical side walls, there was considerable variation in thickness in each sample if the moulds were not completely filled. The shaped articles in general had a minimum thickness near their centre and a maximum thickness near their edges, this variation apparently being derived from the meniscus effect of the composition at the side walls of the mould. The variation in thickness had disadvantages, for example, in handling the formed article and in obtaining consistent and minimal drying times in their preparation. It is an object of the present invention to alleviate these disadvantages.

Accordingly the present invention provides a process for preparing a solid shaped article carrying a predetermined unit quantity of a chemical which process comprises adding to a mould a composition comprising the predetermined amount of chemical and a solution in a solvent of a carrier material inert towards the chemical, the side wall or walls of the mould diverging outwards from the base and making an angle with the vertical of at least 5° at the surface of the composition and the mean depth of the composition in the mould being about 4.0 mm or less, freezing the composition in the mould and then subliming solvent from the frozen composition so as to produce a network of carrier material carrying the chemical.

Preferably the side wall or walls slope outwardly from a substantially flat base and make a constant angle with the vertical, the angle being at least 5°. However, the side walls need not make a constant angle provided that the angle is at least 5° at the surface of the composition. For example the angle below the surface may be less than that at the surface. In addition, or alternatively, the angle above the surface could be greater than the angle at the surface.

The mould is preferably a depression in a sheet of filmic material as hereinabove described. The chemical may be any chemical (including, for example, agricultural or horticultural chemicals or chemical reagents) which it is desired to administer, dispense or utilise in predetermined unit quantities. Preferably the chemical is a pharmaceutical substance and the solid shaped article carrying the predetermined unit quantity of pharmaceutical substance is a pharmaceutical dosage form, particularly a pharmaceutical dosage form suitable for oral administration. By choice of a carrier material that is water soluble or water dispersible it is possible to prepare shaped articles, including pharmaceutical dosage forms, that are capable of being rapidly disintegrated by water, for example, within ten seconds (or preferably 5 seconds) when tested by, for example, the test procedure described in the above mentioned specifications. Examples of suitable carrier materials are given in the above mentioned specifications. For example, the carrier may be formed from polypeptides such as gelatin, particularly gelatin which is partially hydrolysed, e.g. by heating in water. For example, the gelatin may be partially hydrolysed by heating a solution of the gelatin in water, e.g. in an autoclave at about 120° C. for up to 2 hours, e.g. from about 5 minutes to about 1 hour, preferably from about 30 minutes to about 1 hour. The hydrolysed gelatin is preferably used at concentrations of about 1 to 6% weight/vol., most preferably at 2 to 4% e.g. about 3%. Other carrier materials may be used in place of partially hydrolysed gelatin for example polysaccharides such as hydrolysed dextran, dextrin and alginates (e.g. sodium alginate) or mixtures of above mentioned carriers with each other or with other carrier materials such as polyvinyl alcohol, polyvinylpyrrolidine or acacia.

Besides the chemical and the carrier material the composition may contain other additional ingredients. For example, when preparing pharmaceutical dosage forms the composition may include pharmaceutically acceptable adjuvants such as colouring agents, flavouring agents, preservatives and the like. In addition the composition may contain ingredients which aid in the preparation of the shaped articles. For example, the composition may include a surfactant, e.g. Tween 80 [polyoxyethylene (20) sorbitan mono-oleate], to aid in the dispersion of the chemical. The composition may also include ingredients such as fillers (e.g. mannitol, sorbitol) which improve the physical properties of the shaped article.

The solvent for the composition is preferably water but is may contain a co-solvent (such as an alcohol) if it is desired to improve the solubility of the chemical.

The ingredients for the composition may be filled into the mould individually or in admixture, preferably as a mixture comprising the complete composition.

The volume of the composition in the mould is preferably about 3 ml or less (for example, about 0.25 to 1 ml) especially when the shaped article is a pharmaceutical dosage form for oral administration. The depth of the composition in the mould, the cross sectional area of the mould and the angle of the side wall or walls will all affect the volume of the composition. The mould can be, for example, a regular shape such as a circle or a polygon (e.g. a rectangle particularly a square) in horizontal cross section with the area of the section at the base of the mould being less than the area nearer the open top, in view of the sloping sides. Preferably the mould is circular in cross section and the formed shaped article resembles a flat disc having sloping side walls.

In order to keep drying times in the freeze dryer to a minimum it is preferable that the depth of composition in the mould should be less than 3.5 mm, for example, 1.5 ( or more preferably 2) to 2.5 mm. If the depth is below about 1.5 mm the shaped articles tend to be difficult to handle.

The invention further provides a shaped article produced by the process of the invention. The invention particularly provides a solid shaped article produced by freezing a composition comprising a predetermined amount of chemical and a solution in a solvent of a carrier material inert towards the carrier and subliming solvent from the frozen composition so as to produce a network of carrier material carrying the chemical characterised in that the shaped article has a mean thickness of about 4.0 mm or less and has side wall or walls diverging outwards from a bottom surface, said side walls making an angle with the vertical of at least 5° at the upper surface.

In order to investigate the effect of the angle of the side wall or walls had on the variations in thickness of the formed shaped article, a number of blister trays were thermoformed from 200μ UPVC having depressions in them of varying profiles. The depressions were circular in cross section and the profiles, in general, were of inverted truncated cone shape with the side walls making various angles with the vertical. The dimensions of the different profiles together with that of a conventionally formed flat base blister pack (control) are given below:

TABLE I

| Profile | Diameter at base (mm) | Depth of depression (mm) | Upper diameter (mm) | Capacity (ml) | Angle of side wall to the vertical |
|---|---|---|---|---|---|
| 1 | 12.0 | 3 | 13.0 | 0.36 | 9.5° |
| 2 | 11.5 | 3 | 13.0 | 0.35 | 14.0° |
| 3 | 11.0 | 3 | 13.0 | 0.34 | 18.5° |
| 4 | 10.0 | 3.5 | 14.6 | 0.41 | 33.0° |
| 5 | 9.0 | 3.5 | 14.8 | 0.39 | 39.5° |
| 6 | 14.2 | 3.5 | 15.0 | 0.59 | 6.5° |
| control | 14.5 | 6.0 | 15.0 | 1.0 | 2° |

An aqueous composition having the following constitution was prepared:
3% hydrolysed gelatin
3% mannitol B.P. (The 3% hydrolysed gelatin is prepared by suspending 30 g. of powdered gelatin in 800 ml of water, autoclaving it at 121° C. for 60 minutes and adjusting the final volume to 1 liter).

Varying amounts of the composition with and without the addition of a surfactant (1% Tween 80) were added to the depressions (i.e. moulds) of Table I. The compositions were then frozen and the solvent sublimed in a freeze dryer to give solid shaped articles, samples of which, when tested by the procedure in the aforementioned specifications, disintegrated rapidly in water. The dimensions of the shaped articles were determined using a micrometer system and the variation in thickness of the individual samples was calculated. The mean maximum thickness variation for the different samples is shown in the following Table II and is illustrated graphically in FIG. 1 of the accompanying drawings.

TABLE II

| Profile | Angle of side wall to the vertical | Mean maximum thickness variation (mm) |
|---|---|---|
| 1 | 9.5° | 0.8 |
| 2 | 14.0° | 0.57 |
| 3 | 18.5° | 0.4 |
| 4 | 33.0° | 0.48 |
| 5 | 39.5° | 0.42 |
| 6 | 6.5° | 1.07 |
| Control | 2° | 1.88 |

The results show that there was considerable variation in thickness of the samples when the side walls of the mould approached the vertical as, for example in the control. The maximum thickness was at the edge and the minimum thickness was at the centre in these samples, this variation being apparently derived from the meniscus effect although it was not significantly affected by the presence of surfactant. The articles made in depressions in which the side walls made angles with the vertical of considerably more than 5° had much flatter top surfaces. In many of these latter cases the small variation in thickness that did occur was the result of an increased thickness in the centre (a "blip") apparently produced during the freezing procedure. The variations in thickness due to the meniscus effect could be avoided by filling the moulds completely to their upper surface, but, using such full moulds can give rise to further difficulties in that there can be spillage during filling or when the moulds are subsequently handled while the contents are still liquid. In addition, further difficulties can arise if a cover layer is applied over the freeze dried articles in the moulds; the articles may stick to the cover layer if their upper surfaces are substantially level with the upper surfaces of the moulds.

In the present invention a mould is used in which the side wall or walls make an angle with the vertical of at least 5°. The angle with the vertical may be, for example, from 5° to about 40° and the advantage of minimal thickness variation is retained. Especially preferred angles for this advantage as shown in the above profiles, are from about 9° to 40°. However, if the side walls make too big an angle with the vertical the moulds waste unnecessary space in the freeze drier and also the products produced have sharp edges which make them difficult to handle. Accordingly it is preferred that the angle made with the vertical is within the range 9° to 20°, for example 10° to 15°. A particularly preferred angle is about 12°.

FIG. 1 shows the especially preferred angles with the vertical, of the mould side walls, for retaining the advantage of minimal thickness variation.

The following Examples illustrate the invention:

EXAMPLE 1

Pharmaceutical Dosage Forms containing 15 mg oxazepam

| Formulation | |
|---|---|
| Oxazepam | 15 mg |
| Tween 80 BPC | 0.25 mg |
| Mannitol BP | 15 mg |
| 3% hydrolysed gelatin to | 0.5 ml |

The 3% hydrolysed gelatin is prepared by suspending 30 g of powdered gelatin in 800 ml of cold distilled water in a 1 liter flask and autoclaving it at 121° C. for 60 minutes. When cool, the final volume is adjusted to 1 liter.

Oxazepam (30 g) is suspended in 3% hydrolysed gelatin solution containing dissolved mannitol (30 g) and Tween 80 (0.5 g) using ultrasonics for 5 minutes and the suspension made up to 1 liter with 3% gelatin solution. 0.5 ml portions of the suspension are dosed, using an automatic filling machine, into pockets in polyvinyl chloride blister trays. Each of the pockets in the blister tray is of inverted truncated conical shape of 3.5 mm depth, a bottom diameter of 14.5 mm and a top diameter of 16 mm (i.e. the side walls make an angle with the vertical of about 12°). The contents of the pockets are then frozen by passing the trays through a freeze tunnel into which liquid nitrogen is injected.

The blister trays containing the frozen compositions are then transferred to a freeze drier. The pressure is adjusted to 0.5 mm Hg. The temperature of the shelves in the freeze drier is set at 60° C. for 1 hour and then lowered to 40° C. After 2 hours the trays are removed from the freeze drier. A peelable aluminium foil is then sealed to the blister pack around the depressions containing the pharmaceutical dosage forms. The pharmaceutical dosage forms are of substantially uniform thickness and disintegrate rapidly, for example, in two seconds or less, when taken orally.

EXAMPLES 2 TO 11

The procedure of Example 1 is followed to prepare pharmaceutical dosage forms containing the following active ingredients:

| Example | |
|---|---|
| 2 | Oxazepam 30 mg and 50 mg |
| 3 | Lorazepam 1, 2, 2.5 and 4 mg |
| 4 | Temazepam 10 and 20 mg |
| 5 | Lormetazepam 1 mg |
| 6 | Frusemide 40 mg |
| 7 | Bendrofluazide 5 mg |
| 8 | Cyclopenthiazide 0.5 mg |
| 9 | Isosobide dinitrate 2.5, 5 and 10 mg |
| 10 | Indomethacin 25 and 50 mg |
| 11 | Prochlorperazine maleate 50 mg |

EXAMPLE 12

| Formulation | |
|---|---|
| Indole acetic acid | 1 mg |
| Mannitol BP | 15 mg |
| 3% hydrolysed gelatin to | 0.5 ml |

The procedure of Example 1 is followed substituting 2 g of indole acetic acid for the 30 g of oxazepam and omitting the Tween 80. Each of the resulting freeze dried products can be added to 1 liter of water to give a composition useful as a plant growth promoter.

EXAMPLE 13

The procedure of Example 12 is repeated replacing the indole acetic acid by indole butyric acid. Each of the freeze dried products containing 1 mg of indole butyric acid may be added to 1 liter of water to give a composition useful as a rooting growth promoter for plant cuttings.

I claim:

1. A solid shaped article produced by freezing a composition comprising a predetermined amount of a pharmaceutical substance and a solution in a solvent of a carrier material inert towards the pharmaceutical substance and subliming solvent from the frozen composition so as to produce a network of carrier material carrying the pharmaceutical substance characterized in that the shaped article has a substantially uniform thickness of less than about 4.0 mm and has side wall or walls diverging outwards from a bottom surface, said side walls making an angle with the vertical of at least 5° at the upper surface.

2. The shaped article of claim 1 wherein the volume of the composition to be frozen is about 3 ml or less.

3. The shaped article of claim 2 wherein the volume of the composition is about 0.25 to 1 ml.

4. The shaped article of claim 1 wherein the depth of the composition to be frozen is less than 3.5 mm.

5. The shaped article of claim 1 wherein the depth of the composition to be frozen is 1.5 to 2.5 mm.

6. The shaped article of claim 1 wherein the angle with the vertical is from 9° to 20°.

7. The shaped article of claim 1 wherein the angle with the vertical is from 10° to 15°.

8. A solid shape article produced by freezing a composition comprising a predetermined amount of chemical and a solution in a solvent of a carrier material inert towards the chemicals and subliming solvent from the frozen composition so as to produce a network of carrier material carrying the chemical characterized in that the shaped article has a substantially uniform thickness of less than about 4.0 mm and has side wall or walls diverging outwards from a bottom surface, said side walls making an angle with the vertical of at least 5° at the upper surface.

9. The shaped article of claim 2, wherein the angle with the vertical is from 9° to 20°.

10. The shaped article of claim 4, wherein the angle with the vertical is from 9° to 20°.

11. The shaped article of claim 2, wherein the angle with the vertical is from 10° to 15°.

12. The shaped article of claim 4, wherein the angle with the vertical is from 10° to 15°.

* * * * *